(12) United States Patent
Wang et al.

(10) Patent No.: US 7,090,802 B1
(45) Date of Patent: Aug. 15, 2006

(54) SAMPLING ASSEMBLY FOR SIMULTANEOUSLY TESTING A LIQUID BIOLOGICAL SAMPLE FOR A PLURALITY OF HORMONES AND METHOD THEREOF

(75) Inventors: Kai Wang, Bellevue, WA (US); Tong-Yuan Kuo, Taipei (TW); Li-Chuan Chien, Taipei (TW)

(73) Assignee: PhenoGenomics Corporation, Bellevue, WA (US)

( * ) Notice: Subject to any disclaimer, the term of this patent is extended or adjusted under 35 U.S.C. 154(b) by 601 days.

(21) Appl. No.: 10/348,621

(22) Filed: Jan. 29, 2003

Related U.S. Application Data

(63) Continuation-in-part of application No. 10/235,260, filed on Sep. 5, 2002.

(51) Int. Cl.
*G01N 31/22* (2006.01)

(52) U.S. Cl. .................. 422/58; 436/510; 436/514; 436/65; 436/169

(58) Field of Classification Search .............. 435/4, 435/7.1, 287.1–287.2, 288.1, 288.4–288.5, 435/287.7; 436/65, 87, 164, 807, 814, 510; 422/56–58, 61, 68.1, 119
See application file for complete search history.

(56) References Cited

U.S. PATENT DOCUMENTS

| | | | |
|---|---|---|---|
| 5,602,040 A | 2/1997 | May et al. | |
| 5,622,871 A | 4/1997 | May et al. | |
| D379,662 S | 6/1997 | Pearson et al. | |
| D379,663 S | 6/1997 | Pearson et al. | |
| 5,657,762 A | 8/1997 | Coley et al. | |
| D394,317 S | 5/1998 | Carp | |
| 5,804,453 A | 9/1998 | Chen | |
| 6,159,159 A | 12/2000 | Canter et al. | |
| 6,352,862 B1 | 3/2002 | Davis et al. | |
| 6,514,769 B1* | 2/2003 | Lee .......................... 436/518 |
| 6,833,111 B1* | 12/2004 | Robertson et al. ............ 422/58 |
| 2002/0085953 A1* | 7/2002 | Parker ......................... 422/61 |

\* cited by examiner

*Primary Examiner*—Bao-Thuy L. Nguyen
(74) *Attorney, Agent, or Firm*—Patrick J. S. Inouye

(57) ABSTRACT

A sampling assembly for simultaneously testing a liquid biological sample for a plurality of hormones and method thereof are described. A sampling membrane includes a dry porous carrier having a proximal end narrower than a distal end and forming a unidirectional liquid flow channel. The distal end includes a plurality of tines arranged and separated by substantially regular spacing. Each tine defines a dye zone including a dye-tagged antigen-specific antibody at a distal end. The sampling membrane further defines a set of focusing recesses along each side of the unidirectional flow channel end and a set of dispersal recesses between and adjacent to each tine. A plurality of test strips each include a dry porous carrier communicatively attached to the distal end of one such tine. Each test strip forms a unidirectional liquid flow channel and includes a testing zone comprising an antigen-specific antibody located distally from the dye zone.

34 Claims, 12 Drawing Sheets

Figure 7 (con'd).
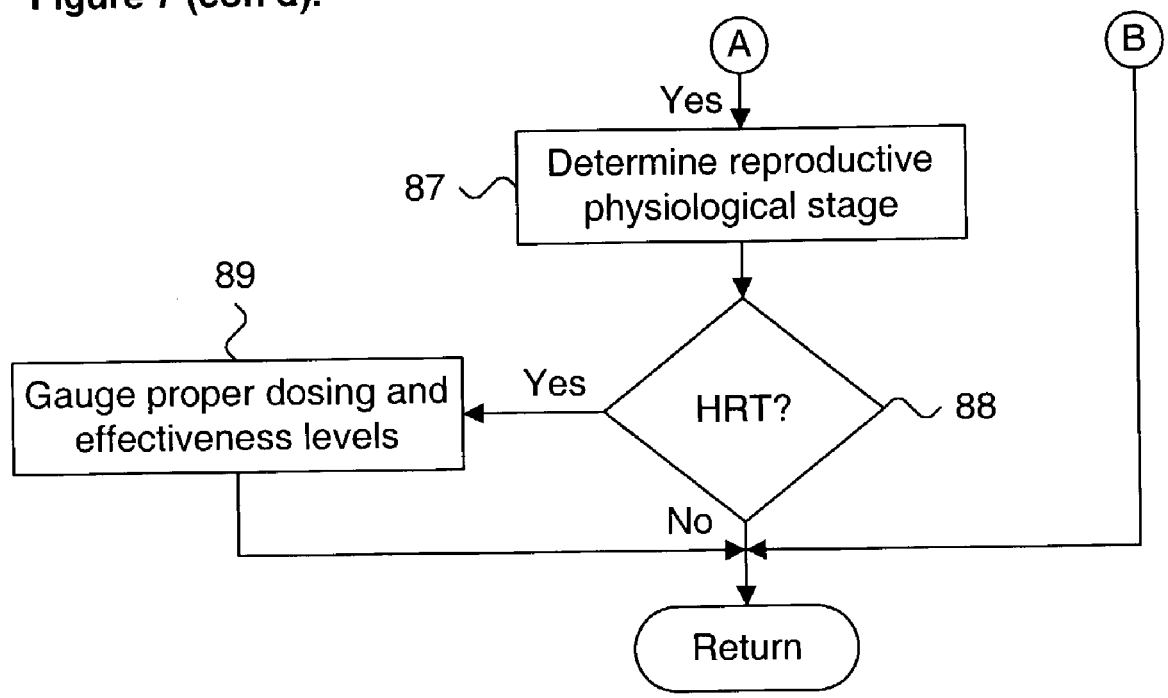

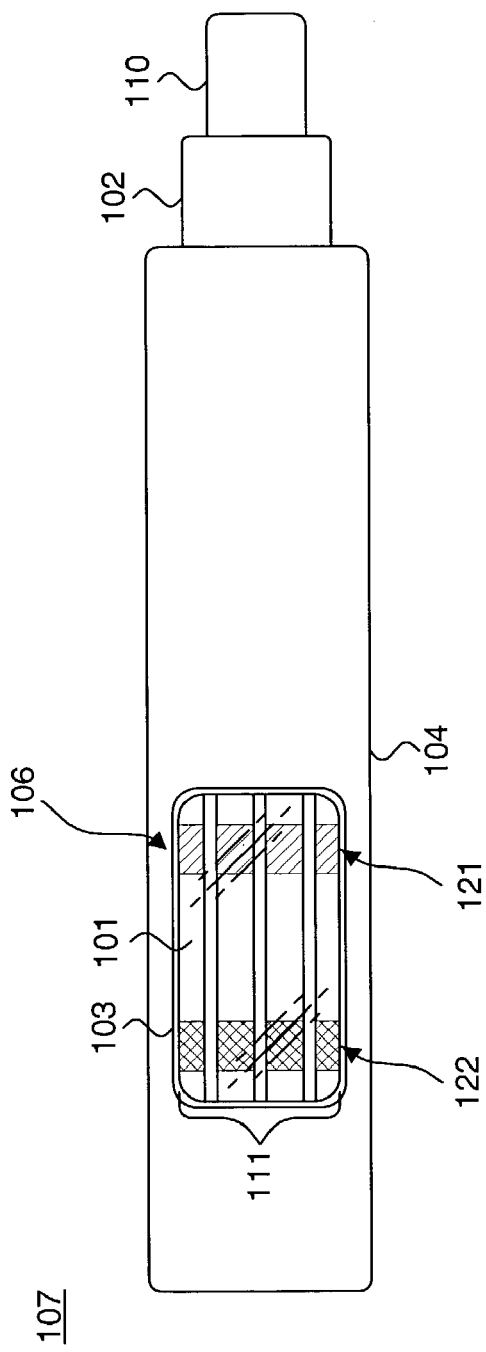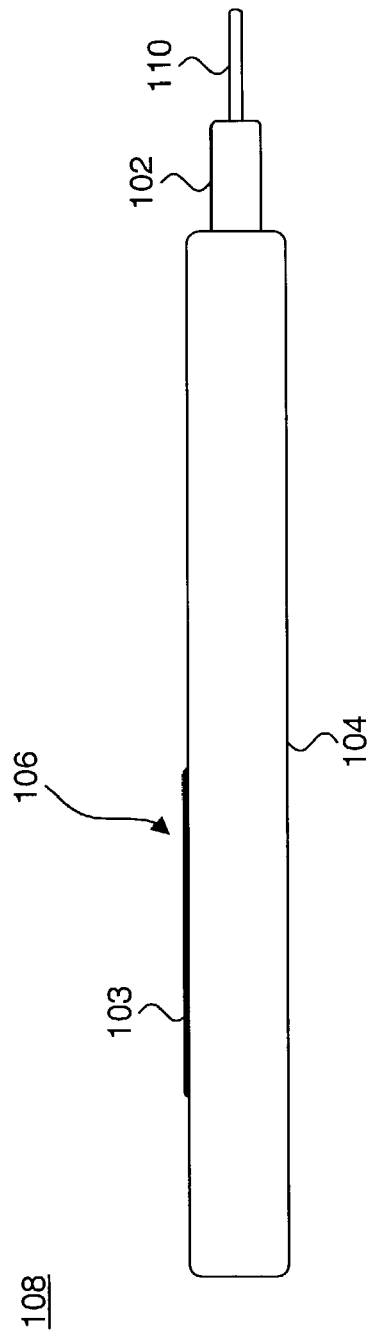
Figure 9.
Figure 10.

SAMPLING ASSEMBLY FOR SIMULTANEOUSLY TESTING A LIQUID BIOLOGICAL SAMPLE FOR A PLURALITY OF HORMONES AND METHOD THEREOF

CROSS-REFERENCE TO RELATED APPLICATION

This patent application is a continuation-in-part of U.S. patent application Ser. No. 10/235,260, filed Sep. 5, 2002, pending, the disclosure of which is incorporated by reference.

FIELD OF THE INVENTION

The present invention relates in general to female physiological stage determination and monitoring, and, in particular, to a sampling assembly for simultaneously testing a liquid biological sample for a plurality of hormones and method thereof, including those hormones associated with the menstrual cycle, ovulation, pregnancy and menopause.

BACKGROUND OF THE INVENTION

The female ovulation, or menstrual, cycle occurs every 28 to 30 days on average, measured from the onset of menstruation. Three significant events can occur in conjunction with the menstrual cycle: ovulation, pregnancy, and menopause. Ovulation marks the beginning of a period of fertility while pregnancy follows from the fertilization of an ovum. Menopause marks the final menstrual event. Determining and monitoring ovulation, pregnancy and menopause is important.

Conception in a human female can only occur during periods of fertility, typically in the 24 through 36 hours following ovulation. For couples desiring conception, accurately determining the time of ovulation is critical. Conversely, certain religious, ethnic and social groups prohibit the use of active forms of contraception and rely on abstinence during periods of female fertility as the sole means of birth control. At around age 50, most women begin to experience a number of endocrinal changes as menopause approaches due to a loss of ovarian follicular activity. A period of hormonal changes can last up to four years, during which time many women experience adverse symptoms, including hot flashes, night sweats, sleeplessness, vaginal dryness and mood swings. Hormone replacement therapy, providing estrogen and progestin in combination, or estrogen replacement therapy, providing estrogen alone, can be prescribed to treat and counter potential undesired side effects arising from menopause or premature ovarian failure. Hormone replacement therapy will be used herein to refer to both therapies involving combined estrogen and progestin treatment as well as estrogen treatment alone.

Presently, up to 20% of menopausal women use some form of hormone replacement therapy in the United States. Recent studies on hormone replacement therapy suggest an increase in the risk for cancer and heart disease and recommend that the levels of hormones dosed be closely monitored and adjusted on an individual basis. Safely providing appropriate hormone replacement therapy requires an accurate historical record of menstrual cycle-related hormonal levels to provide an accurate basis for initial and ongoing dosing levels.

The menstrual cycle begins at menarche and ends at menopause, and proceeds in four stages. The first stage, menstruation, lasts four to five days and is characterized by the shedding of the endometrial lining of the uterus and menstrual discharge. The second stage, pre-ovulation, or the estrogenic phase, lasts from 10 to 16 days, during which time a follicle (egg sac) containing an ovum forms inside one of the ovaries. The third stage, ovulation, lasts from 24 to 36 hours, occurring about Day 14 in a 28-day cycle, and takes place when the follicle ruptures, releasing a mature ovum into a Fallopian tube and thence into the uterus. The last stage, the luteal or progestational phase, takes about 11 to 14 days following ovulation, during which time the ruptured follicle, or corpus luteum, withers and is reabsorbed by the body if fertilization has not occurred. If pregnancy occurred, the level of human chorionic gonadotrophin (hCG) increases six to ten days following ovulation.

The menstrual cycle is controlled primarily by an interplay of four hormones: estrogen, progesterone, follicle stimulating hormone (FSH), and luteinizing hormone (LH). About mid-cycle, just prior to ovulation, the level of estrogen rises, triggering a surge in LH, accompanied by a transient rise in basal body temperature. These events signal that ovulation is imminent. Thus, LH level and basal body temperature are most often monitored to determine fertility.

Similarly, the onset of menopause is characterized by significant endocrinal changes, including a decrease in the production of estrogen, progesterone and testosterone, followed by a measurable increase in FSH at the cessation of ovarian follicular activity. Generally, a woman has reached menopause when FSH blood level rises above 30 to 40 MIU/ml. Estrogen, as estradiol or estrone, is also sometimes measured in determining whether menopause has occurred.

Reliance on a single factor, particularly a specific hormone, is misplaced. Hormone levels, and therefore the menstrual cycle, and menopause, can be affected heavily by external and physiological factors and can be erratic and difficult to predict. These factors include physiological stress, health and well-being, drugs, ovarian cysts, sexually transmitted diseases, and others. Thus, the menstrual cycle and menopause are best monitored by observing the interplay of all four hormones, rather than just LH or basal body temperature.

Measuring multiple hormones, though, is time-consuming and difficult in a non-clinical environment. Individual tests are required to detect the level of each hormone and the presence of each will depend on the point in the menstrual cycle at which measurement occurs. In addition, a single battery of hormone tests represents at best a snapshot of hormonal levels and is meaningless without applying a historical perspective of previous hormone levels over the present and past menstrual cycles.

In the prior art, historical menstrual cycle data has been used for determining and monitoring reproductive physiological stages based on a lay understanding of ovulation. The calendar or rhythm method of family planning relies on pinpointing the time of ovulation based on past menstrual cycles to increase the chances of, or to avoid, conception. Due to the variance inherent in menstrual cycles, though, the calendar method is marginal at best and often unreliable.

Similarly, the basal body temperature method attempts to identify the time of ovulation based on the transient body temperature increase which generally precedes ovulation, such as described in U.S. Pat. No. 5,657,762 to Coley et al, issued Aug. 19, 1997, the disclosure of which is incorporated by reference. However, basal body temperature can be skewed by other, non-ovulation related events, rendering basal body temperature measurements an unreliable indicator. As well, the shift in body temperature can be out of synchrony with ovulation by as much as three to six days instead of the expected 24 to 36 hours.

Ferning tests are also used to detect the period of ovulation, such as described in U.S. Pat. No. 6,159,159 to Canter et al, issued Dec. 12, 2000, the disclosure of which is incorporated by reference. Ferning occurs in dried saliva observed four to six days prior to ovulation and is roughly correlated to increases in chloride content. Determining the presence of ferning requires a low-magnification lens and is qualitative. The basis of the ferning test has not been scientifically proven and the subjectivity of the ferning test undermines the reliability of determining ovulation using this method.

Analogously, the onset of menopause can be tested at home using a blood test that measures circulating FSH levels. Menopause onset can also be tested based on FSH levels in the urine, typically read at a level of 25 IU/L, which corresponds directly with blood serum levels. However, FSH level alone can only serve at best as a general guide to the onset of menopause.

Presently, numerous devices are available commercially for testing hormone levels in a non-clinical environment, particularly at home. These devices typically perform an assay of a readily-obtainable sample of biological material, such as urine, blood or saliva, and provide a result probative of a relative hormone level. However, at best, each test results in a qualitative indicator based a subjective reading. Single result outcomes, such as provided by such at-home tests, provide limited information. Moreover, aberrations between single reading tests are common and multiple tests must be performed to obtain a more comprehensive picture of overall hormonal levels.

For example, U.S. Pat. No. 5,602,040 to May et al., issued Feb. 11, 1997, the disclosure of which is incorporated by reference, describes an analytical test device useful in pregnancy testing. A dry porous carrier protrudes from an enclosing hollow casing to receive a liquid biological sample. A labeled specific binding reagent becomes freely mobile within the porous carrier when moistened and a liquid sample permeates into a second zone comprising an unlabeled specific binding reagent for the same analyte, thereby enabling the extent to which the labeled reagent becomes bound in the second zone to be observed. In addition, a device arranging multiple discrete bodies of porous solid phase material in parallel to obtain multiple analytical results from a single sample simultaneously is described. However, the May device fails to disclose providing unidirectional liquid flow channels facilitating uniform sample distribution and deposition.

Therefore, there is a need for an approach to monitoring multiple hormones on a preferably regular basis throughout the menstrual cycle to determine fertility through ovulation, pregnancy and the onset of menopause. Preferably, such an approach would be easily used in a non-clinical environment and avoid a reliance on test results from a single hormone.

There is a further need for an approach to maintaining a historical data bank of hormone levels throughout one or more menstrual cycles. Preferably, such an approach would provide an accurate weighing of the various factors relating to a menstrual cycle and for use in determining and monitoring reproductive physiological stages, in medical diagnoses, and in hormone or estrogen replacement therapy during menopause.

Therefore, there is a need for a testing approach for providing accurate readings of a plurality of hormones obtained from a single liquid biological sample, preferably configurable as a lay test for use in a non-clinical at-home environment. Preferably, such an approach would facilitate historical tracking of multiple hormone levels recorded over one or more menstrual cycles.

SUMMARY OF THE INVENTION

The present invention provides a sampling assembly for simultaneously testing a liquid biological sample for a plurality of hormones and method thereof and related physiological status through evaluation of a plurality of hormones. A sample of bodily fluid is analyzed using a set of bioprobes or similar measurement instrument to determine the relative levels of five preferred hormones, comprising estrogen, progesterone, FSH, hCG, and LH. Alternatively, a multi-strip apparatus for performing an assay of a liquid biological sample for a plurality of hormones to determine the relative hormone levels. The samples are collected preferably on a regular basis throughout one or more successive menstrual cycles and are stored as data records in a database. Following the completion of the monitoring of at least one full menstrual cycle, subsequent samples of the multiple hormones are evaluated and trends in the historical data are analyzed. Fertility is determined based on the correspondence of an observed rise in estrogen followed by a spike in LH and an increase in FSH, preferably within the ranges of 100 to 500 pg/ml, 20 to 120 mIU/ml, and 3 to 40 mIU/ml, respectively.

An embodiment provides a sampling assembly for simultaneously testing a liquid biological sample for a plurality of hormones and method thereof. A sampling membrane includes a dry porous carrier having a proximal end narrower than a distal end and forms a unidirectional liquid flow channel proceeding from the proximal end along a longitudinal axis. The distal end of the sampling membrane includes a plurality of tines arranged and is separated by substantially regular spacing parallel to the longitudinal axis. Each tine defines a dye zone including a dye-tagged antigen-specific antibody at a distal end. The sampling membrane further defines a set of focusing recesses along each side of the unidirectional flow channel end and a set of dispersal recesses between and adjacent to each tine. The sampling membrane further includes a plurality of test strips. Each test strip includes a dry porous carrier communicatively attached to the distal end of one such tine. Each test strip further forms a unidirectional liquid flow channel proceeding from the proximal end along the longitudinal axis and further includes a testing zone comprising an antigen-specific antibody located distally from the dye zone of the one such tine.

A further embodiment provides a multi-strip testing device for simultaneously assaying a liquid biological sample for a plurality of hormones and method thereof. A sampling assembly includes a sampling membrane and a plurality of test strips. The sampling membrane includes a dry porous carrier forming a unidirectional liquid flow channel proceeding from a proximal end along a longitudinal axis to a distal end. The proximal end includes a sampling zone. The distal end of the sampling membrane forms a shoulder wider than the proximal end and defines a set of focusing recesses along each side. The sampling membrane further includes a plurality of tines arranged and separated by substantially regular spacing parallel to the longitudinal axis and defines a set of dispersal recesses between and adjacent to each tine. Each tine defines a dye zone including a dye-tagged antigen-specific antibody at a distal end. Each test strip includes a dry porous carrier communicatively attached to the distal end of one such tine and arranged and separated by substantially regular spacing parallel to the longitudinal axis. Each testing zone further includes an antigen-specific antibody located distally from the dye zone of the one such tine and forms a unidirectional liquid flow channel proceeding from the proximal end along the longitudinal axis. A casing defines a substantially hollow cavity extending continuously along the longitudinal axis from a proximal end and sized to fixedly receive the sampling assembly with an aperture exposing the sampling zone and disposed to facilitate liquid flow downstream along the unilateral flow channel.

A further embodiment provides a multi-strip apparatus for simultaneously testing a liquid biological sample for a plurality of hormones and method thereof. Sampling means include dry porous carrier means having a proximal end narrower than a distal end and means for forming a unidirectional liquid flow distally along a longitudinal axis. The distal end of the sampling means includes a plurality of concentrating means arranged and separated by substantially regular spacing and defines dye-tagging means including a dye-tagged antigen-specific antibody. The sampling means further defines a set of liquid flow focusing means along each side of the forming means and a set of liquid flow dispersal means between and adjacent to each concentrating means. A plurality of testing means are included. Each testing means includes dry porous carrier means communicatively attached to the distal end of one such concentrating means and means for forming a unidirectional liquid flow distally along the longitudinal axis. Each testing means further includes assaying means including an antigen-specific antibody located distally from the dye-tagging means. Housing means define a substantially hollow cavity extending continuously along the longitudinal axis and sized to fixedly receive the sampling means and the testing means. The housing means further defines means for exposing the proximal end of the sampling means and disposed to facilitate liquid flow.

A further embodiment provides a system and method for determining and monitoring reproductive physiological stages in a human female by monitoring a plurality of hormones using a multi-strip sampling assembly. A sampling assembly includes a sampling membrane and a plurality of test strips. The sampling membrane includes a dry porous carrier having a proximal end narrower than a distal end and forms a unidirectional liquid flow channel proceeding from the proximal end along a longitudinal axis. The distal end of the sampling membrane includes a plurality of tines arranged and separated by substantially regular spacing parallel to the longitudinal axis. Each tine defines a dye zone including a dye-tagged antigen-specific antibody at a distal end. The sampling membrane further defines a set of focusing recesses along each side of the unidirectional flow channel end and a set of dispersal recesses between and adjacent to each tine. Each test strip includes a dry porous carrier communicatively attached to the distal end of one such tine. Each test strip further forms a unidirectional liquid flow channel proceeding from the proximal end along the longitudinal axis and further includes a testing zone including an antigen-specific antibody located distally from the dye zone of the one such tine. A testing instrument reads the testing zones for at least two samples of bodily fluid for a plurality of hormones. Each sample is obtained at different times during a given menstrual cycle. An evaluator analyzes individual levels of a plurality of hormones in each sample through protein-based antibody-antigen analysis. The individual hormone levels are stored and physiological state is determined, including fertility, using trending data based on evaluating the stored individual hormone levels for a same type of hormone from each of the at least two samples over the given menstrual cycle.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 9 is a top view of the casing used by the sampling assembly of FIG. 8.

FIG. 10 is a side view of the casing used by the sampling assembly of FIG. 8.

DETAILED DESCRIPTION

Figure 1A:
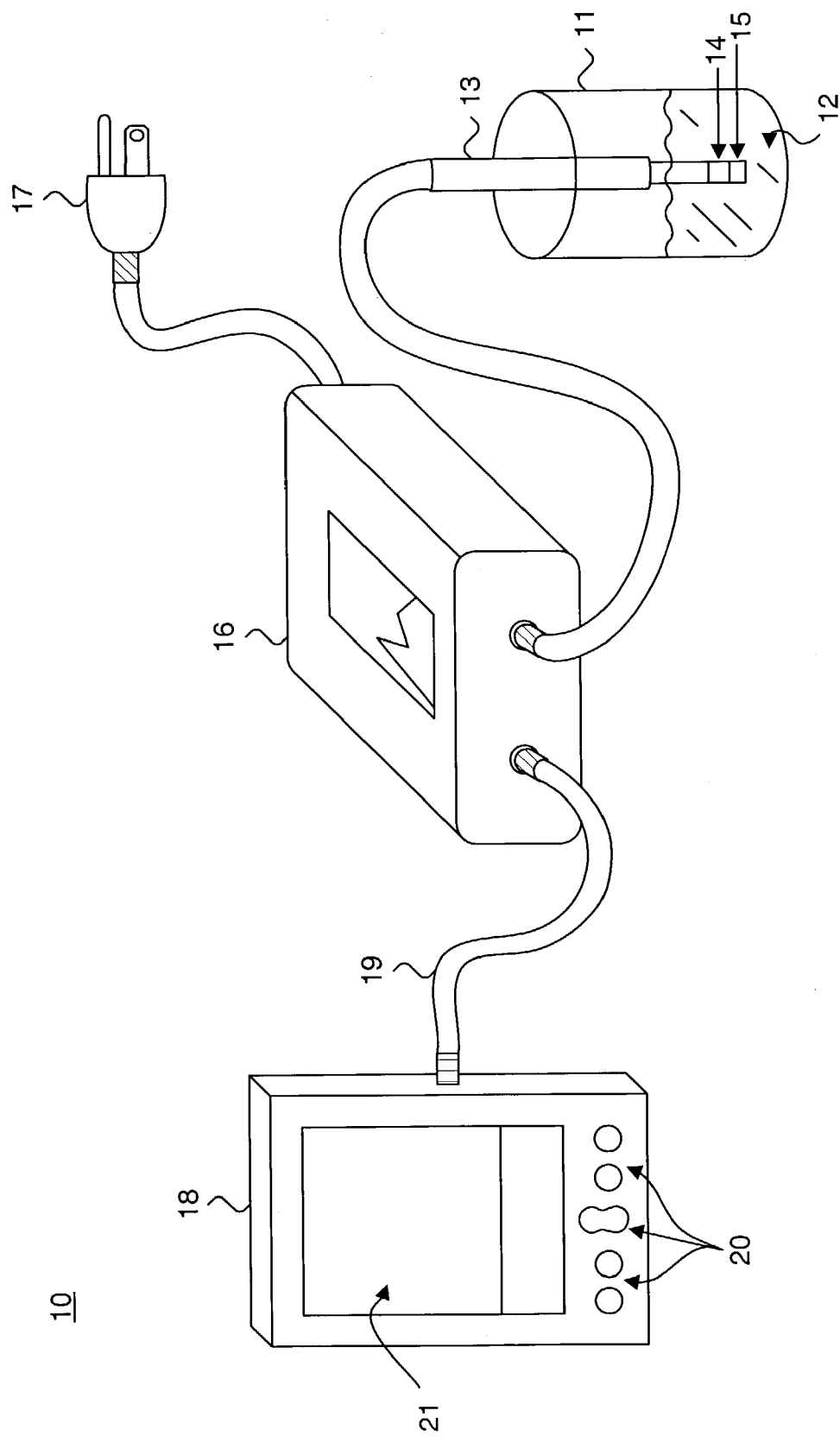
FIG. 1A is a block diagram showing a system for determining and monitoring reproductive physiological stages in a human female by monitoring a plurality of hormones using a fiber optic biosensor, in accordance with the present invention.

FIG. 1A is a block diagram showing a system 10 for determining and monitoring reproductive physiological stages in a human female by monitoring a plurality of hormones using a fiber optic biosensor, in accordance with the present invention. A container 11 containing a body fluid sample 12, such as urine, is tested using a fiber optic biosensor 13. An exemplary fiber optic biosensor 13 is described in U.S. Pat. No. 5,804,453 to Chen, issued Sep. 8, 1998, the disclosure of which is incorporated by reference. The fiber optic biosensor 13 is a testing instrument that incorporates a plurality of hormone-sensitive fiber optic probe sets, each with a reactive layer by which individual hormone level can be measured through specific interactions. A supporting layer 14, such as polystyrene, and a protein layer 15, such as an antibody against a specific hormone, are present on a distal end of the fiber optic biosensor 13 to interact with hormones in the body fluid sample 12. Each hormone in the sample 12 interacts with the antibody protein layer 15 in a specific hormone-dependent fashion, thereby allowing a determination of the presence and concentration of the specific hormone.

The fiber optic biosensor 13 is interfaced to a spectrometer 16, which includes a power connection 17. An exemplary spectrometer 16 is the S-2000 Miniature Fiber Optic Spectrometer from Ocean Optics, Inc., Dunedin, Fla. The spectrometer 16 analyzes a diffracted incident beam received through the proximal end of the fiber optic biosensor 13 and includes a high-sensitivity linear charge coupled device (CCD) array for measuring wavelength absorbance, reflection and emission, as is known in the art. The fiber optic biosensor 13 and spectrometer 16 generate the raw data from which hormone levels can be identified and detected.

Figure 1B:
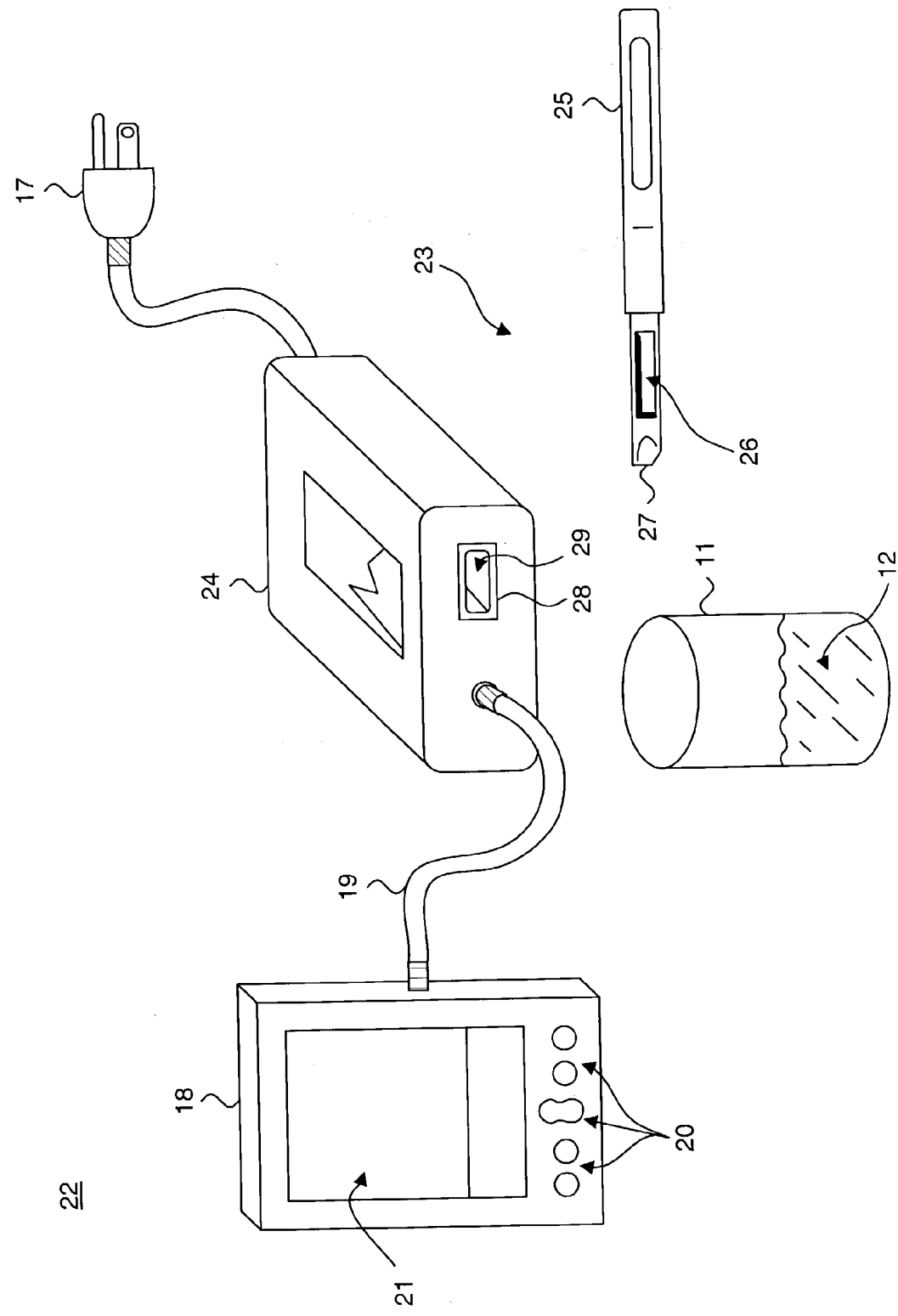
FIG. 1B is a block diagram showing a system for determining and monitoring reproductive physiological stages in a human female by monitoring a plurality of hormones using a test strip sensor, in accordance with a further embodiment of the present invention.

FIG. 1B is a block diagram showing a system 22 for determining and monitoring reproductive physiological stages in a human female by monitoring a plurality of hormones using a test strip sensor 23, in accordance with a further embodiment of the present invention. The container 11 containing the body fluid sample 12, such as urine, is tested using the test strip sensor 23. A test strip 26 on a distal end 27 of a strip biosensor 25 is exposed to the body fluid sample 12. An exemplary strip biosensor is described in U.S. Pat. No. 5,622,871 to May et al., issued Apr. 22, 1997, the disclosure of which is incorporated by reference.

A plurality of antibodies against various hormones are present on the test strip 26. The test strip 26 contains a supporting layer, such as nitrocellulose, and reaction regions, such as antibodies against several hormones. Each hormone from the sample 12 interacts with a specific antibody located on a designated reaction region of the test strip 26, thereby allowing a determination of the presence and concentration of the specific hormone.

Following exposure of the test strip 26 to the body fluid sample 12, the distal end 27 of the strip biosensor 25 is inserted 29 into a test strip slot 28 on a miniature scanner 24, which includes a power connection 17. The miniature scanner 24 analyzes the light absorbance and generates the raw data from which hormone levels can be identified and detected. Alternatively, the strip biosensor 25 could be electronically coupled (not shown) to a spectrometer 16 (shown in FIG. 1B) to directly analyze the light absorbance, as would be recognized by one skilled in the art.

The spectrometer 16 or miniature scanner 24 are communicatively interfaced via an adapter cable 19 or, alternatively, via a wireless communication protocol (not shown) to a conventional computer system (not shown) or a portable computing device 18. The conventional computer system and portable computing device 18 both include a set of controls 20 and a display 21 for providing outputs to a user. An exemplary conventional computer system is a Windows-based personal computer, such as manufactured by Compaq Computer Corporation, Austin, Tex. An exemplary portable computing device 18 is the Palm m515 handheld, sold by Palm, Inc., Santa Clara, Calif., or the iPAC Pocket PC 3970, sold by Compaq Computer Corporation, Houston, Tex.

The conventional computer system and computing device 18 both include a processor for performing program instructions and memory and peripheral storage in which to store program code and data, as is known in the art. As further described below with reference to FIG. 3, the conventional computer system or computing device 18 execute an evaluator to analyze hormone levels measured by the spectrometer 16 for comparison to historical data and for use in determining and monitoring reproductive physiological stages and medical diagnosis. The system 10 operates in accordance with a sequence of process steps, as further described below with reference to FIG. 4.

In combination, the fiber optic biosensor 13, spectrometer 16 and computing device 18, or, alternatively, the test strip sensor 23, miniature scanner 24 and computing device 18 form spectral analysis testing means. Other means for detecting and analyzing the presence and levels of hormones in a body fluid sample 12 could be used, including a sampling assembly, such as described in related, commonly owned U.S. Design Pat. Application, Ser. No. D493,893 S, filed Jan. 21, 2003, pending, the disclosure of which is incorporated herein by reference, and as further described below beginning with FIG. 8, as well as litmus, chemical reagent, and spectral analytical devices, as are known in the art. The personal computing device 18 could alternatively be any form of general purpose, programmed computing device consisting of a central processing unit (CPU), random access memory (RAM), non-volatile secondary storage, network or wireless interfaces, and peripheral devices, including user interfacing means, such as a keyboard and display. Program code, including software programs, and data are loaded into the RAM for execution and processing by the CPU and results are generated for display, output, transmittal, or storage.

Figure 2:
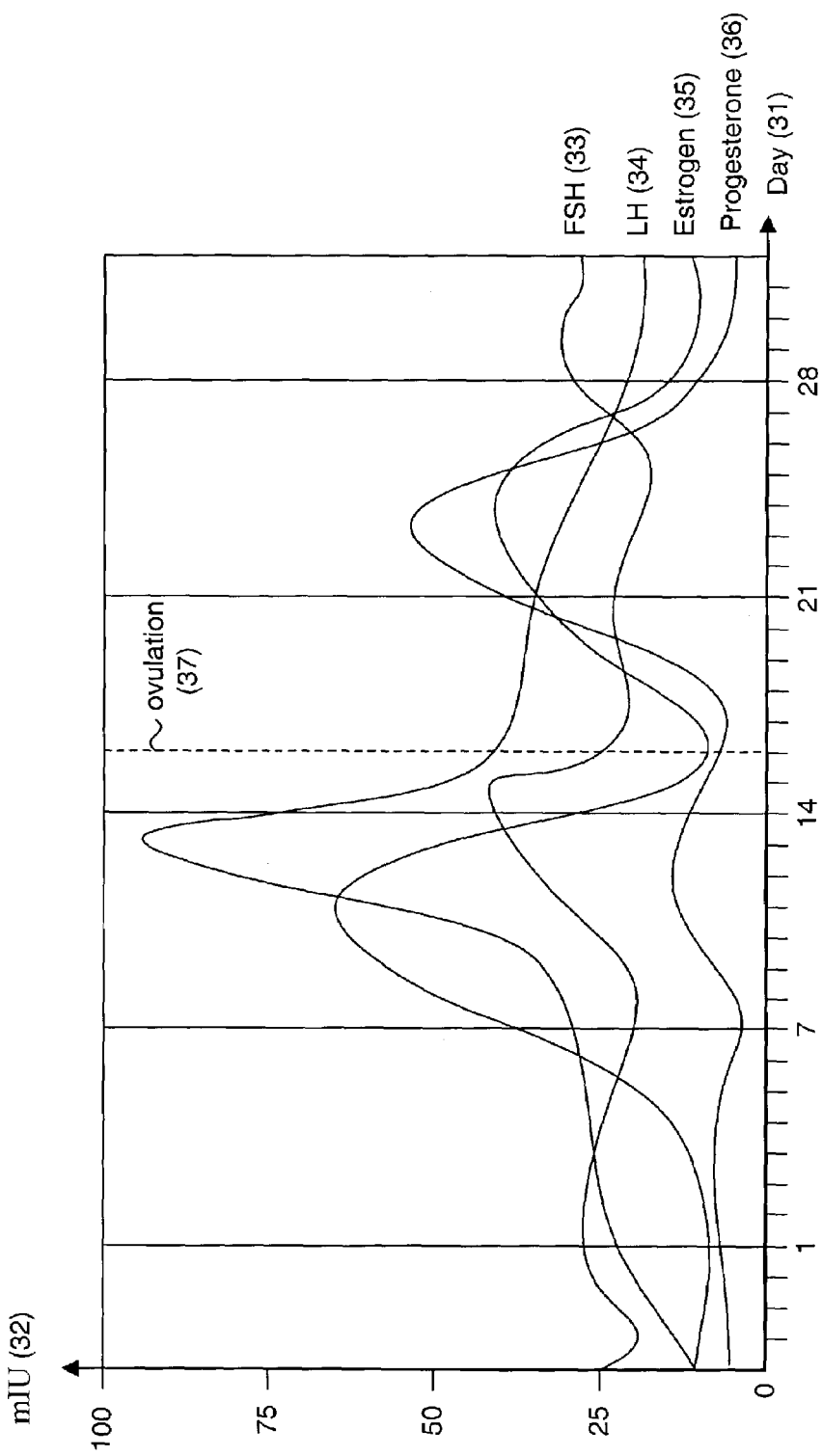
FIG. 2 is a graph showing, by way of example, a typical cycle of female reproductive hormones.

FIG. 2 is a graph 30 showing, by way of example, a typical cycle of female reproductive hormones. The graph 30 visualizes the relative hormone levels throughout an average 28-day menstrual cycle. The x-axis 31 defines the day of the cycle. The y-axis 32 defines the hormone level in milli international units (mIU).

The four hormones shown, FSH 33, LH 34, estrogen 35, and progesterone 36, follow a fairly regular pattern of interaction throughout a menstrual cycle. Prior to the onset of menstrual bleeding on Day 1, estrogen 35 and progesterone 36 levels drop sharply to signal the uterus that pregnancy has not occurred. FSH 33 stimulates follicle or corpus luteum development in the ovaries. Around Days 5 to 7, one of the stimulated corpus luteums becomes dominant and begins secreting large amounts of estrogen 35. In turn, the estrogen 35 stimulates the endometrial lining of the uterus, which becomes thicker and enriched for receiving a fertilized egg. Around mid-cycle, about Day 8, the estrogen 35 stimulates a large release of LH 34, which causes the corpus luteum to rupture and expel the mature ovum into the Fallopian tube. Ovulation 37 typically occurs within 72 hours following the spike in LH 34.

Upon rupture, the corpus luteum begins secreting progesterone 36 to prepare the endometrial lining for implantation of a fertilized egg. If fertilized, a small amount of human chorionic gonadotrophin (hCG) hormone is released, which keeps the corpus luteum viable and secreting estrogen 35 and progesterone 46. If not fertilized, the corpus luteum withers, causing estrogen 35 and progesterone 36 levels to drop. The uterus sheds the endometrial lining and menstruation begins. The level of FSH 33 begins to rise again in the absence of estrogen 35, to start another menstrual cycle.

Figure 3:
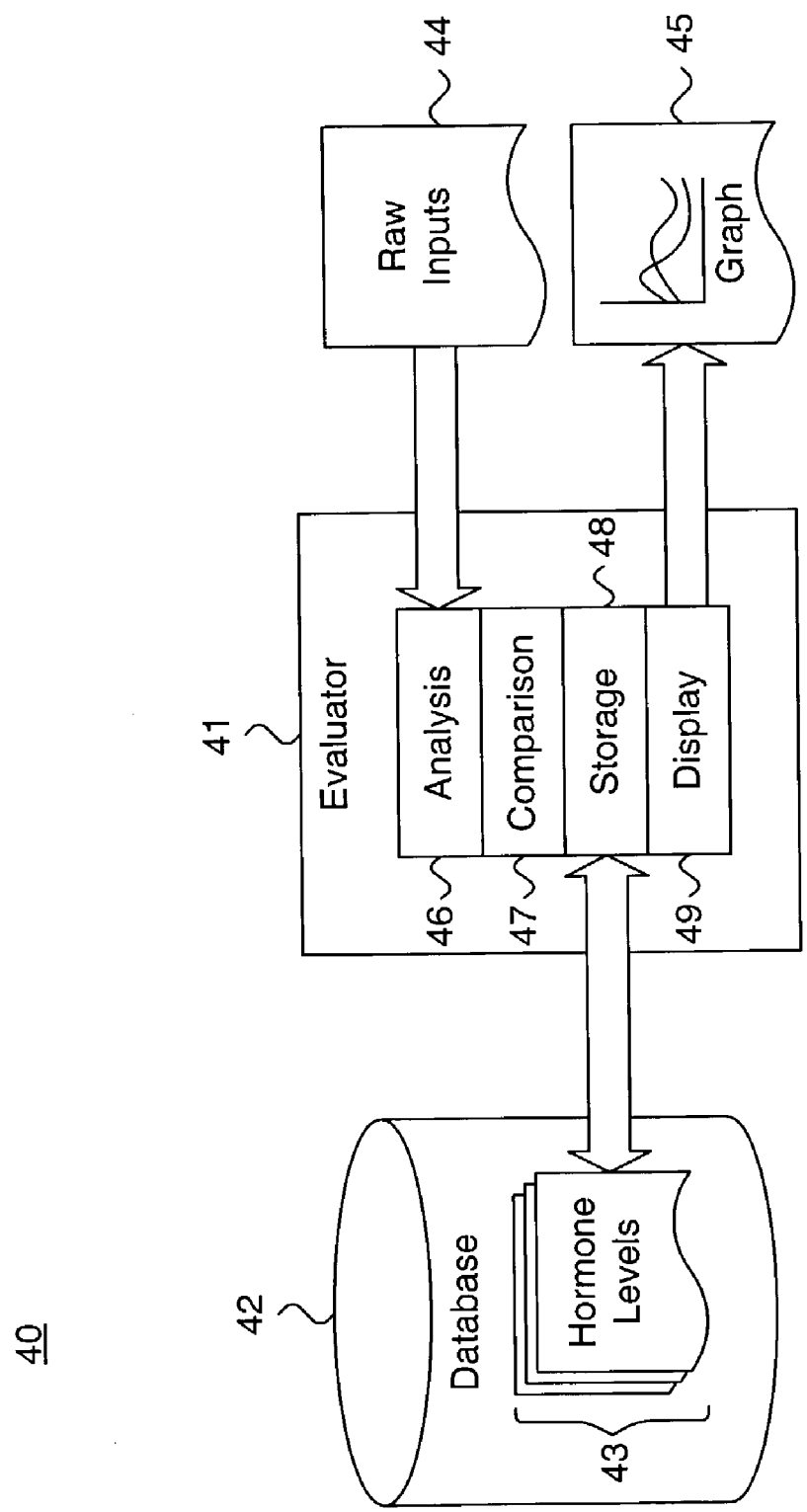
FIG. 3 is a block diagram showing the software modules implementing an evaluator for execution by the system of FIG. 1.

FIG. 3 is a block diagram showing the software modules 40 implementing an evaluator 41 for execution by the system of FIG. 1. The evaluator 41 is presented as program code to the CPU of the portable computing device 18 (shown in FIG. 1), as is known in the art. The evaluator 41 includes four modules: analysis 46, comparison 47, storage 48, and display 49. The analysis module 46 receives raw inputs 44 containing the degree of wavelength shift on the refractive light from spectrometer 16 caused by the interaction of hormone to the bioprobe 13. The raw inputs 44 are analyzed to determine the presence and relative levels of hormones, such as FSH, LH, estrogen, progesterone, and hCG. The analyzed hormone levels 43 are stored as data records in a database 42 via the storage module 48. The comparison module 47 evaluates the hormone levels 43 to determine fertility based on the point in the menstrual cycle. Finally, the display module 49 generates output and graphical data 45 showing the hormone levels 43 over time and other information.

The analysis module 46 determines each hormonal level through an analysis of the degree of wavelength shift received via the reagent layer 15 on the fiber optic biosensor 13. The hormone levels are also compared to expected ranges of hormone levels. Preferably, at least one menstrual cycle is monitored before determining and monitoring reproductive physiological stages to create a baseline of observed hormone levels. By way of example, on Day 3 of the menstrual cycle, FSH should be in the range of approximately 3–40 mIU/ml, estrogen in the range of approximately 25–75 pg/ml, and LH in the range of approximately 5–20 mIU/ml.

Figure 4:
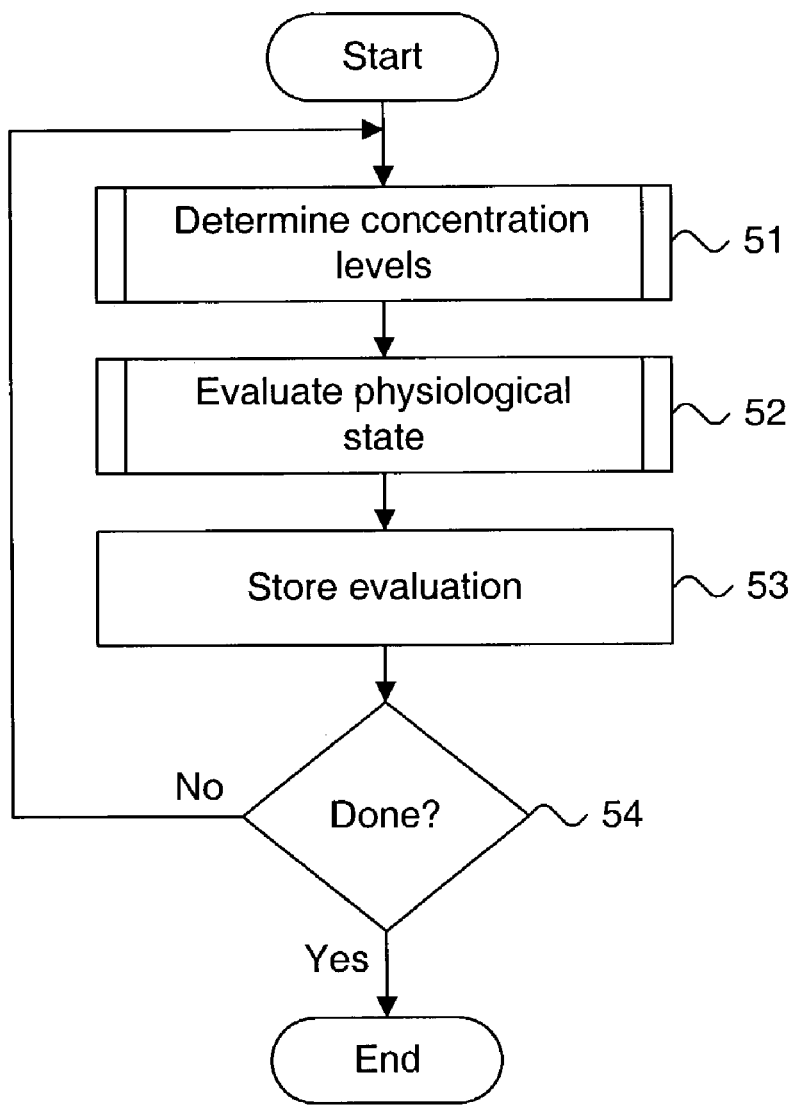
FIG. 4 is a flow diagram showing a method for determining and monitoring reproductive physiological stages in a human female by monitoring a plurality of hormones, in accordance with the present invention.

FIG. 4 is a flow diagram 50 showing a method for determining and monitoring reproductive physiological stages in a human female by monitoring a plurality of hormones, in accordance with the present invention. The method is performed each time a sample 12 (shown in FIG. 1) is received and preferably on a regular basis throughout successive menstrual cycles.

First, the concentration levels of the hormones, such as LH, FSH, estrogen, hCG, and progesterone, are determined (block 51), as further described below with reference to FIG. 5. Next, the physiological state of the user is evaluated (block 52), as further described below with reference to FIG. 6. The physiological state includes a finding of fertility window (ovulation), pregnancy and menopause. The evaluation is stored with the hormone levels 43 in the database 42 (shown in FIG. 3) (block 53). If the evaluation is not complete (block 54), the evaluation continues as before. Otherwise, the method terminates.

Figure 5:
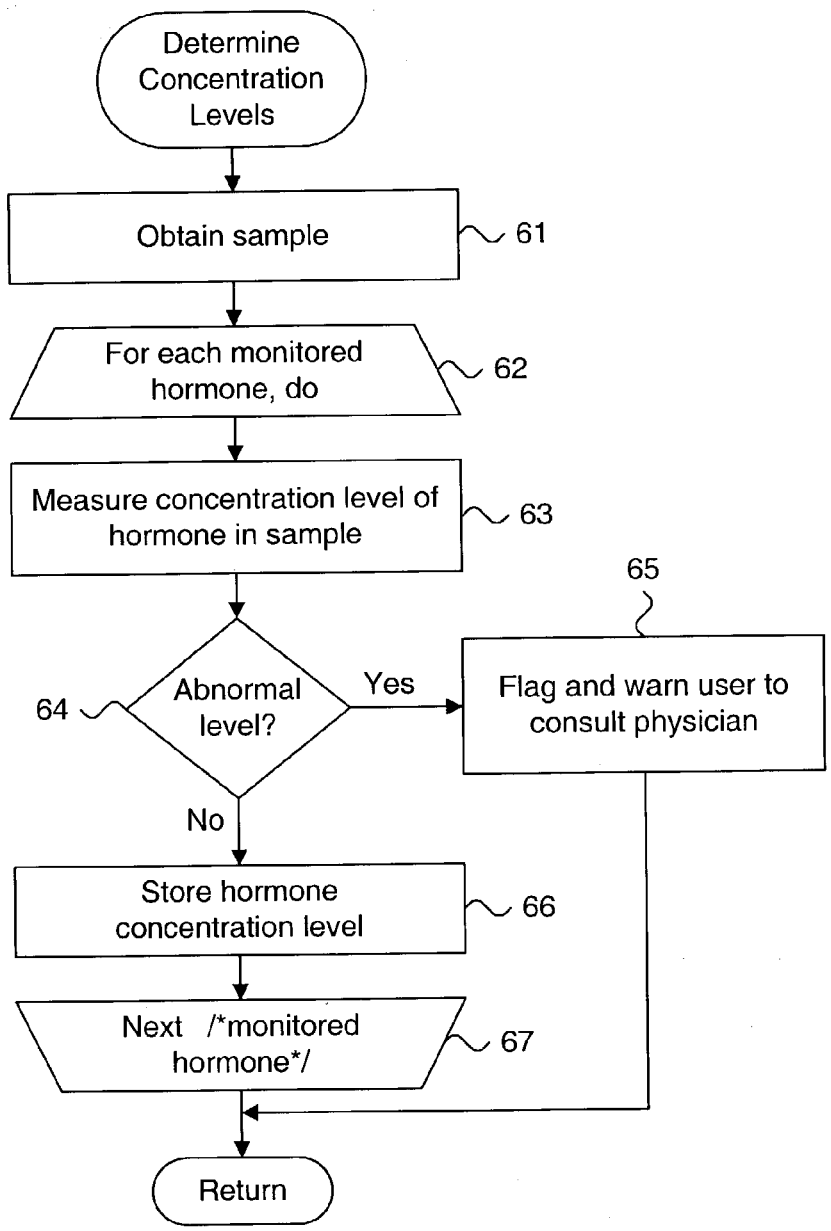
FIG. 5 is a flow diagram showing a routine for determining concentration levels for use in the method of FIG. 4.

FIG. 5 is a flow diagram showing a routine for determining concentration levels 60 for use in the method of FIG. 4. The purpose of this routine is to measure and store hormone level readings received via the fiber optic biosensor 13 as processed by the spectrometer 16 or miniature scanner 24 (shown in FIGS. 1A and 1B, respectively).

First, a sample is obtained (block 61) as raw inputs 44 (shown in FIG. 3). For each of the monitored hormones, such as, LH, FSH, estrogen, hCG, and progesterone, an iterative evaluation cycle is performed (block 62–67). During each iteration (block 62), the concentration level of the hormone in the sample 12 is measured (block 63), as described above with reference to FIG. 3. If the concentration level is abnormal (block 64), the measurement is flagged and the user is warned to consult a physician (block 65). In the described embodiment, an abnormal level is defined as exceeding 50% of the normal range. Otherwise, if the concentration level is normal (block 64), the hormone concentration level is stored (block 66) as a data record 43 in the database 42 (shown in FIG. 3). Processing continues with the next hormone (block 67), after which the routine returns.

Figure 6:
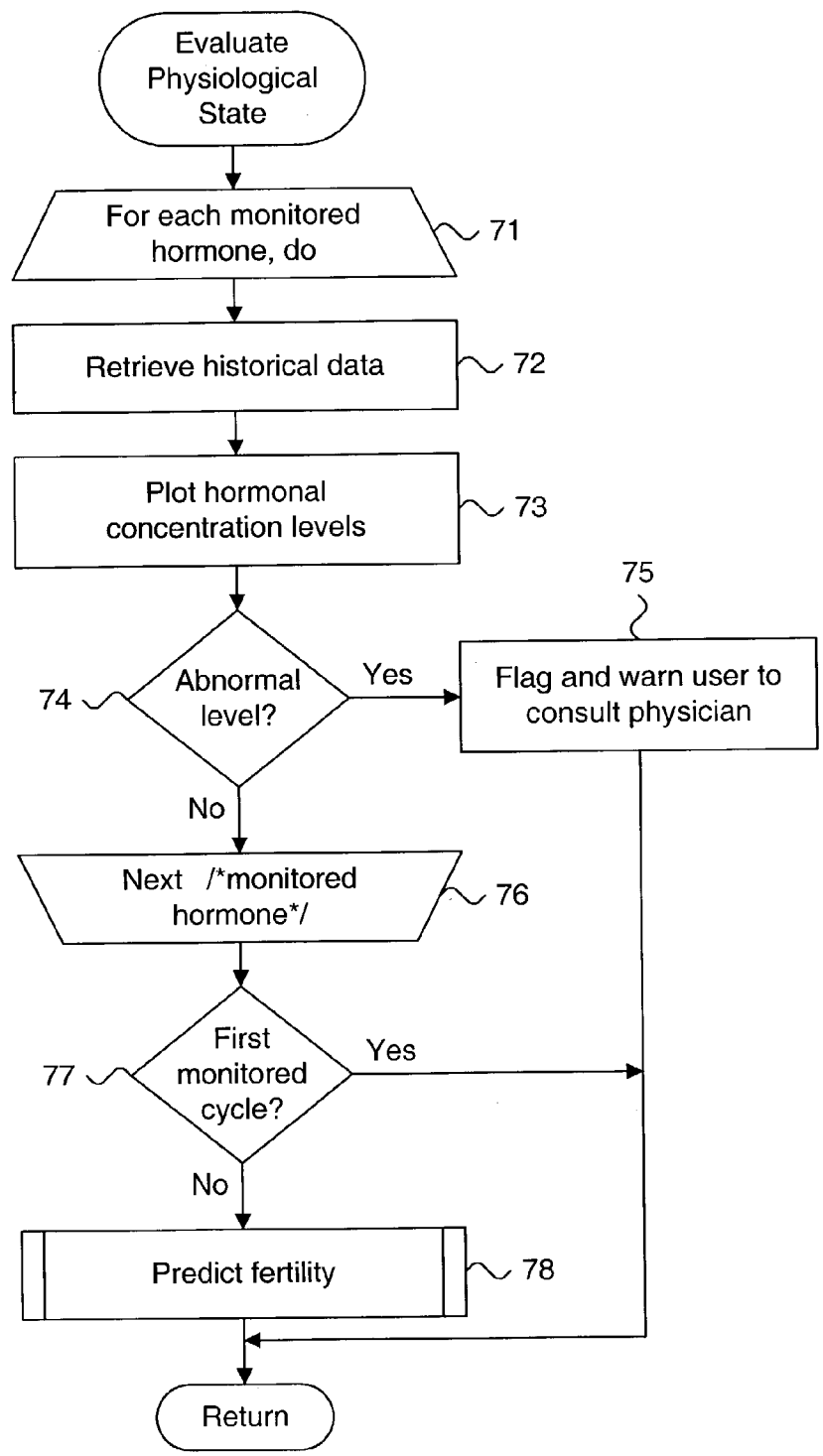
FIG. 6 is a flow diagram showing a routine for evaluating physiological state for use in the method of FIG. 4.

FIG. 6 is a flow diagram showing a routine for evaluating physiological state 70 for use in the method of FIG. 4. The purpose of this routine is to analyze the current sample for a given user against the historical data maintained in the database 42 to determine fertility window (ovulation), pregnancy, menopausal stages, and for use in medical diagnosis.

First, each monitored hormone is evaluated in an iterative analysis loop (blocks 71–76). During each iterative loop (block 71), the historical data for the hormone is retrieved (block 72) from the database 42 as hormone level data records 43. The hormonal concentration levels are plotted (block 73) to determine trending data. For instance, if the level of hCG is steadily increasing after the ovulation, the rise may indicate pregnancy has occurred. Similarly, a large increase in estrogen could signal the onset of an increase in LH. If the hormone levels are abnormal (block 74), the hormone levels are flagged and the user is warned to consult with a physician (block 75). In the described embodiment, an abnormal level is defined as exceeding 50% of the normal range or abnormal increase or decrease based on the trending data stored in database 42. Otherwise, if the hormone levels are normal (block 74), processing continues with the next monitored hormone (block 76). Upon completion of the evaluation of each of the monitored hormones (blocks 71–76), if the current menstrual cycle is not the first monitored cycle (block 77), fertility window is predicted (block 78), as further described below with reference to FIG. 7. Preferably, at least one menstrual cycle is monitored before determining and monitoring reproductive physiological stages to create a baseline of observed hormone levels. The routine then returns.

Figure 7:
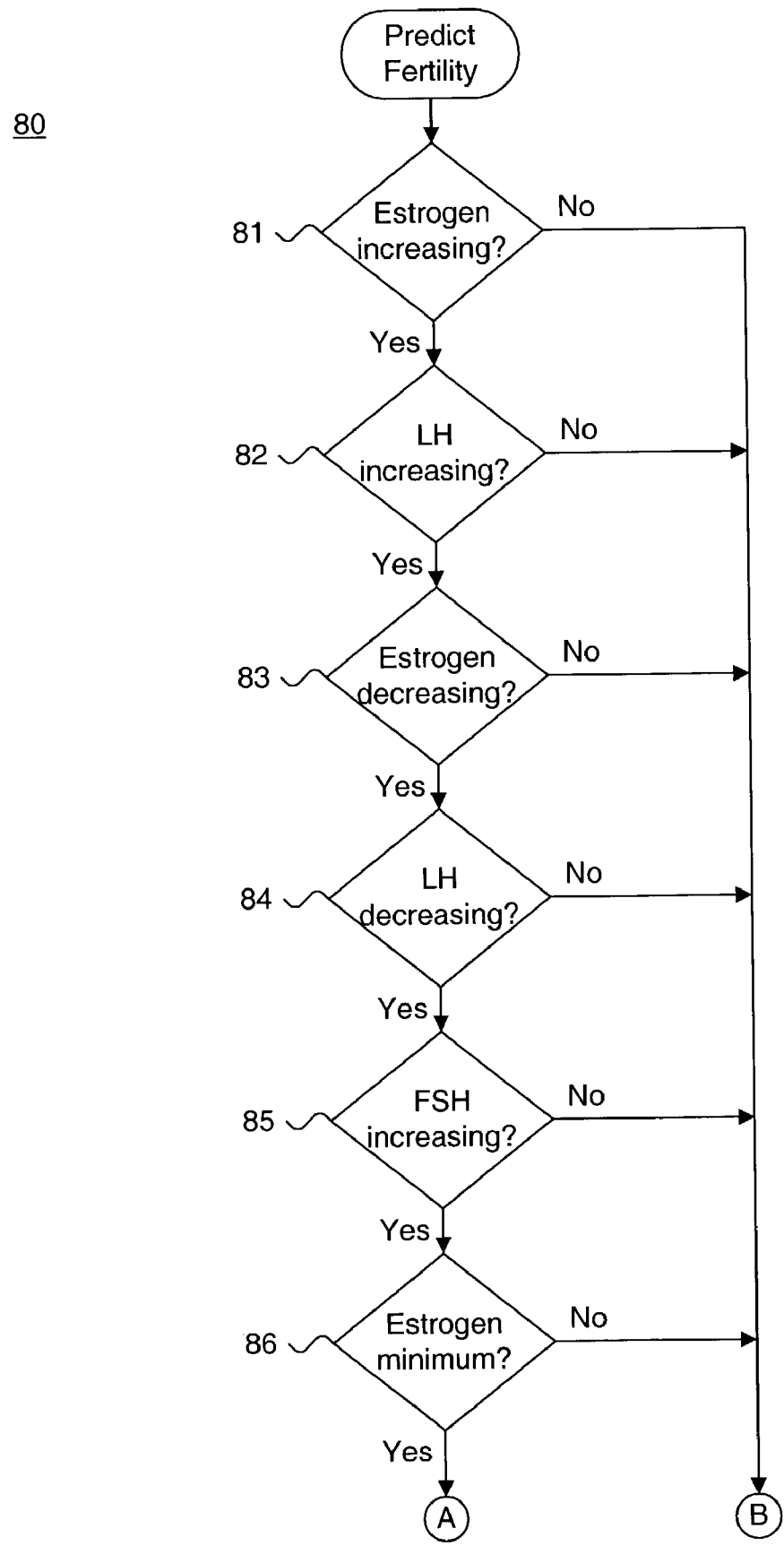
FIG. 7 is a flow diagram showing a routine for predicting fertility for use in the routine of FIG. 6.

FIG. 7 is a flow diagram showing a routine for predicting fertility window 80 for use in the routine of FIG. 6. The purpose of this routine is to accurately determine the time of occurrence of ovulation and, thence, fertility, based on a temporal analysis of hormone level trends in the historical data for the hormone levels data records 43 stored in the database 42 instead of the absolute level of a single hormone. The routine tracks the general trends for multiple hormones throughout a given menstrual cycle.

First, if the estrogen level has increased or is increasing (block 81) compare to the data 43 stored in database 42, typically in the range of approximately 100 pg/ml to 500 pg/ml, the user may have been in or be in the pre-ovulation phase. Next, if the LH level has increased or is increasing (block 82), typically in the range of approximately 20 mIU/ml to 120 mIU/ml, the surge of LH preceding ovulation may be imminent or underway. Thus, if the estrogen level has decreased or is decreasing (block 83) following a rise in FSH level, typically in the range of approximately 3 mIU/ml to 40 mIU/ml, the LH surge has occurred and the estrogen level is on the decline, signaling ovulation within the next 24 to 36 hours.

In the described embodiment, a fertility window occurring from about two days prior through two days following ovulation is used, although other time ranges are possible, as would be recognized by one skilled in the art. For instance, if the estrogen, FSH and LH levels continue to decline and progesterone is increasing in the range of approximately 1 to 2 ng/ml, the ovulation date has already passed and the fertility window missed. Note a peak of progesterone level can be used to project the next cycle of by ovulation date, which usually occurs 21 days after reaching the peak of progesterone level. Upon completion of the foregoing trending analyses (block 81–86), a reproductive physiological stage, that is, fertility window (ovulation), pregnancy and menopause, including premature ovarian failure, is determined (block 87).

In the described embodiment, the following general guidelines are applied to determine pregnancy and menopause, including premature ovarian failure, although one skilled in the art would recognize that other guidelines are possible, either in addition to or in combination with the foregoing. During pregnancy, the level of hCG doubles about every 24 to 36 hours and the level of hCG increases from approximately 2 to 50 mIU/ml at about three weeks from the last menstrual period to approximately 6,000 to 250,000 mIU/ml at about 7 weeks from the last menstrual period. Menopause and premature ovarian failure can be detected by observing a follicle stimulating hormone level in the range of approximately 20 mIU/ml to 200 mIU/ml in conjunction with a low estrogen level occurring lower than 30 pg/ml.

For menopausal women, if the individual is undergoing hormone or estrogen replacement therapy treatments (HRT) (block 88), the proper dosing and effectiveness levels are gauged (block 89). In the described embodiment, the levels of estrogen, progesterone, luteinizing hormone, and follicle stimulating hormone are monitored to gauge the proper dosing and effectiveness levels of estrogen and progesterone in hormone or estrogen replacement therapy treatments. Lastly, the routine then returns.

Figure 8:
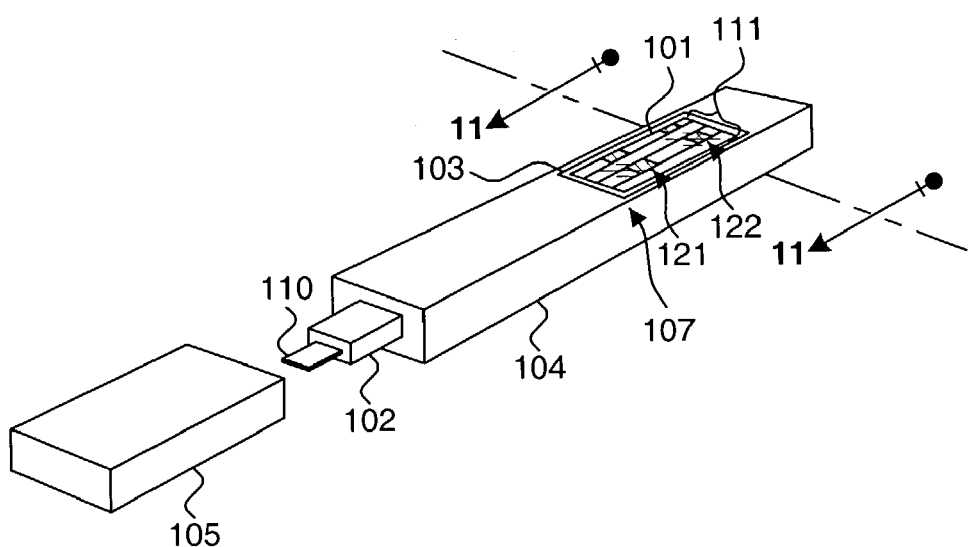
FIG. 8 is a perspective view showing a sampling assembly, plus casing, for simultaneously testing a liquid biological sample for a plurality of hormones, in accordance with the present invention.

FIG. 8 is a perspective view 100 showing a sampling assembly 110, plus casing 104, for simultaneously testing a liquid biological sample for a plurality of hormones, in accordance with the present invention. The casing 104 houses the sampling assembly 101, as further described below beginning with reference to FIG. 12, and is preferably constructed using a moisture-impervious material, such as plastic or nylon. The casing 104 is optionally provided with a cover 105, also constructed of the same moister-impervious material, and is formed to removably fit over a sampling assembly holder 102 formed on a proximal end of the casing 104.

The casing 104 both protects and fixably mounts the sampling assembly 101. The sampling assembly 101 simultaneously tests a liquid biological sample for a plurality of hormones and includes a sampling membrane 110 and a plurality of test strips 111. The sampling membrane 110 is exposed through the sampling assembly holder 102 on the proximal end of the casing 104 and is disposed to facilitate deposit of liquid biological samples.

Each test strip 111 is communicatively attached to the sampling membrane 110 and includes a testing zone 121 containing an antigen-specific antibody and, preferably, a control zone 122 containing an antigen-neutral antibody. The antibodies in the testing zone 121 and control zone 122, if provided, interact with a dye-tagged antigen-specific antibody (not shown) provided on the sampling membrane 110 to provide a visual indication of the presence and relative amounts of hormones when moistened by the liquid biological sample. Preferably, the casing 104 includes an aperture window 103 formed distally along the casing to provide visual inspection 106 of the testing zones 121 and control zones 122, if provided.

FIG. 9 is a top view 107 of the casing 104 used by the sampling assembly 101 of FIG. 8. In the described embodiment, the aperture window 103 is located over the testing zones 121 and control zones 122, if provided, of the test strips 111. Optionally, the aperture window 103 includes a transparent cover constructed of a moisture-impervious material, such as plastic or glass. When moistened by the deposit of a liquid biological sample, the antigen-specific antibodies in each testing zone 121 and antigen-neutral antibodies in each control zone 122, if provided, react with the dye-tag antigen-specific antibody provided on the sampling membrane 110 to create a visual indication, preferably displayed in shades of one or more colors, of the presence and relative amounts of a hormone reactive to each antibody. The visual indication can be viewed through the aperture window 103 and compared to a reading chart to provide interpretive results, as is known in the art.

The aperture window 103 also enables the testing zones 121 and control zones 122, if provided, to be read and analyzed by a spectral analyzer, such as a miniature scanner 24 (shown in FIG. 1). Following liquid biological sample deposition, the distal end of the casing 104 is inserted 29 into the test strip slot 28 on the miniature scanner 24. The miniature scanner 24 analyzes the light absorbance of each testing zone 121 and generates log data from which hormone levels can be identified and measured. A further optional mode enables a more precise assay of hormones by providing the log data to a conventional computer system or computing device 18 for analysis and comparison to historical data.

FIG. 10 is a side view 108 of the casing 104 used by the sampling assembly 110 of FIG. 8. Liquid biological samples are deposited on a proximal end of the sampling membrane 110. Both the sampling membrane 110 and test strips 111 are formed of dry porous carriers and form unilateral liquid flow channels that urge and disperse the deposited liquid biological sample into the casing 104. In the described embodiment, the casing 104 is formed as a testing device that can easily be held in a hand and operated without exposing the user to direct contact with the liquid biological sample.

Figure 11:
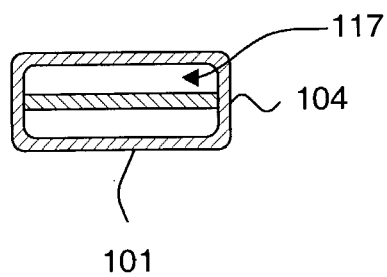
FIG. 11 is a transverse cross-sectional view of the casing used by the sampling assembly of FIG. 8.

FIG. 11 is a transverse cross-sectional view 109 of the casing 104 used by the sampling assembly 101 of FIG. 8. The casing 104 defines a hollow cavity 117 extending continuously along a longitudinal axis and sized to fixably receive the sampling assembly 101. The sampling assembly 101 is held in place by the sides and ends of the casing 104. In the described embodiment, the casing 104 is formed as a closeable housing configured to fixably clamp at least two sides of the sampling assembly 101 in a manner disposed to maintain substantially unencumbered exposure of the top and bottom surfaces.

Figure 12:
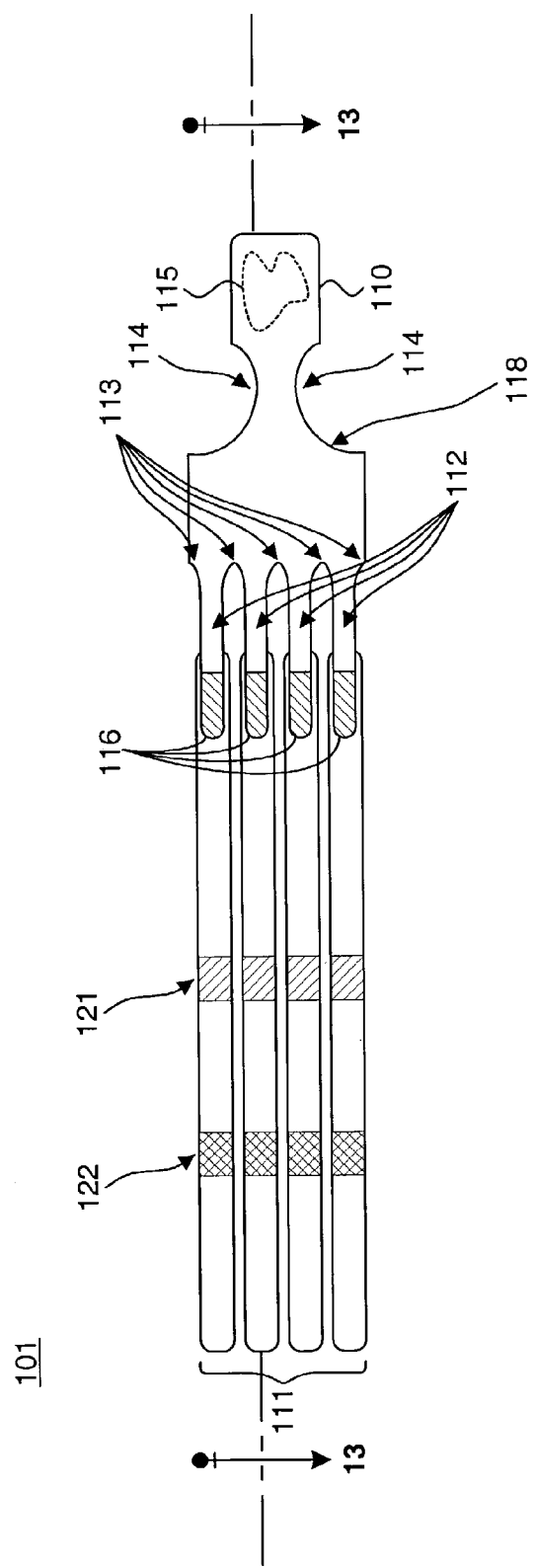
FIG. 12 is an elevational view showing the sampling assembly of FIG. 8.

FIG. 12 is an elevational view showing the sampling assembly 101 of FIG. 8. The sampling assembly 101 consists of a sampling membrane 110 and a plurality of tests strips 111. The sampling membrane 110 and each test strip 111 are constructed of a dry porous carrier, such as a nitrocellulose carrier, such as described in U.S. Pat. No. 5,602,040, to May et al., issued Feb. 11, 1997, the disclosure of which is incorporated by reference.

The sampling membrane 110 is formed to facilitate the distribution and deposition of a liquid biological sample evenly over each test strip 111 by taking advantage of the capillary effect. The proximal end of the sampling membrane 110 is narrower than the distal end of the sampling membrane 110, which includes a pair of shoulders 118 which project beyond the sides of the proximal end. The sampling membrane 110 is also formed to create a unidirectional liquid flow channel preceding from the proximal end along a longitudinal axis. Liquid biological samples are deposited on a sampling zone 115 formed on the proximal end of the sampling membrane 110 and disposed external to the sampling assembly holder 102 (shown in FIG. 8). A set of focusing recesses 114 are formed along each side of the unidirectional flow channel to create a capillary effect on a liquid flow. In the described embodiment, the focusing recesses 114 are shaped as semi-circular cavities, although other shapes could be used, as would be recognized by ones skilled in the art.

Each test strip 111 is communicatively attached to the distal end of the sampling membrane 110. A set of tines 112 are formed at the distal end of the sampling membrane 110, arranged and separated by substantially regular spacing with one tine 112 per test strip 111. A set of dispersal recesses 113 is formed between and adjacent to each tine 112 to further provide a capillary effect to liquid flow. In the described embodiment, each dispersal recess 113 is shaped as a semi-ovoid cavity, although other shapes could be used, as would be recognized by one skilled in the art. Both sets of recesses 113 and 114 facilitate distribution and deposition of liquid biological samples evenly over each test strip 111 through capillarity.

Figure 13:
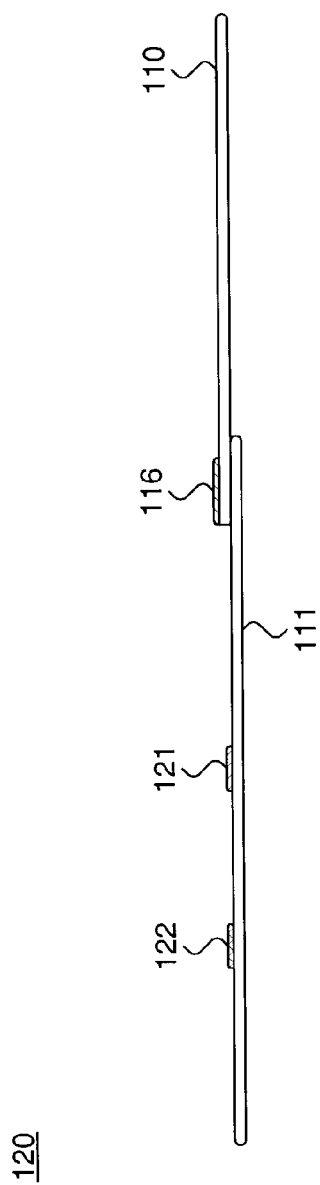
FIG. 13 is a lateral side cross-sectional view of the sampling assembly of FIG. 8.

FIG. 13 is a lateral side cross-sectional view 120 of the sampling assembly 110 of FIG. 8. Each test strip 111 is communicatively attached to the distal end of one of the tines 113 of the sampling membrane 110. A dye zone 116 is defined at the distal end of each tine 113 arranged to overlap the attached test strip 111. In the described embodiment, each dye zone 116 consists of a dye-tagged antigen-specific antibody. A testing zone 121 is defined at a location located distally from the dye zone 116 of the attached tine 113. In the described embodiment, each testing zone 121 consists of an antigen-specific antibody sensitized to detect the presence and level of a hormone, such as estrogen, progesterone, LH and FSH. Preferably, each test strip 111 also defines a control zone 122 located distally from the testing zone 121 of the test strip 111. In the described embodiment, each control zone 122 consists of an antigen-neutral antibody. Other combinations of antibodies are possible in lieu of dye tagging combinations to effect similar interpretive results usable as a hormone assay, as would be recognized by one skilled in the art.

Operationally, a liquid biological sample, such as urine, is deposited on the sampling assembly 101 at the sampling zone 106. The liquid flows downstream from the sampling zone 106 along the unidirectional flow channel and is focused by the focusing recesses 114 into a concentrated uniform liquid flow. Upon clearing the focusing recesses 114, the liquid biological sample disperses over the wider distal end of the sampling membrane 110 and is dispersed by the dispersal recesses 113 to flow along each tine 112. As the liquid biological flow sample disperses onto each test strip 111, the liquid biological sample moistens each dye zone 116 and uniformly flows along the tests strips 111 to encounter the testing zones 121 and, if provided, control zones 122. The antigen-specific antibodies of each testing zone 121 bind with the hormonal proteins and create a dye-tagged label indicating the presence and relative amount of each respective hormone. In addition, the antigen-neutral antibodies of the control zones 122 bind with the dye-tagged antigen to confirm that the sampling is adequate and uniformly determined. Other uses and combinations of the sampling assembly 101 and various configurations of testing, analysis, and assaying instruments are feasible, as would be recognized by one skilled in the art.

While the invention has been particularly shown and described as referenced to the embodiments thereof, those skilled in the art will understand that the foregoing and other changes in form and detail may be made therein without departing from the spirit and scope of the invention.

What is claimed is:

1. A sampling assembly for simultaneously testing a liquid biological sample for a plurality of hormones, comprising:
    a sampling membrane comprising a dry porous carrier having a proximal end narrower than a distal end and forming a unidirectional liquid flow channel proceeding from the proximal end along a longitudinal axis to the distal end, the distal end of the sampling membrane comprising a plurality of tines arranged and separated by substantially regular spacing parallel to the longitudinal axis, each tine having a dye zone comprising a dye-tagged hormone-specific antibody at a distal end; wherein the sampling membrane further comprises a set of focusing recesses along each side of the unidirectional flow channel and a set of dispersal recesses between and adjacent to each tine; and
    a plurality of test strips, each test strip comprising a dry porous carrier communicatively attached to the distal end of each tine; wherein each test strip further forms a unidirectional liquid flow channel proceeding from the proximal end along the longitudinal axis and further comprises a testing zone comprising an immobilized hormone-specific antibody located distally from the dye zone of each tine.

2. The sampling assembly according to claim 1, further comprising:
    a casing comprising a substantially hollow cavity extending continuously along a longitudinal axis from a proximal end and sized to fixedly receive the sampling membrane and the plurality of test strips; the casing further comprising an aperture on the proximal end exposing the proximal end of the sampling membrane and disposed to facilitate liquid flow downstream along the unidirectional liquid flow channels.

3. The sampling assembly according to claim 2, further comprising:
    a cover comprising a substantially hollow cavity disposed to removably cover the exposed proximal end of the sampling membrane.

4. The sampling assembly according to claim 2, further comprising:
    an aperture window formed along a side of the casing that is disposed to provide visual inspection of the testing zone.

5. The sampling assembly according to claim 2, further comprising:
    at least one pylon formed within the hollow cavity near a distal end of the casing and fixedly holding the distal end of at least one test strip.

6. The sampling assembly according to claim 2, wherein the casing comprises a moisture-impervious material.

7. The sampling assembly according to claim 1, wherein each test strip further comprises a control zone comprising an antibody that is not specific for the hormones in the sample and that is located distally from the testing zone of each tine.

8. The sampling assembly according to claim 1, wherein each focusing recess comprises a semi-circularly-shaped cavity and each dispersal recess comprises a semi-ovoidly-shaped cavity.

9. The sampling assembly according to claim 1, wherein the dye-tagged hormone-specific antibody comprises an antibody specific for a hormone selected from the group consisting of estrogen, progesterone, luteinizing hormone (LH), and follicle stimulating hormone (FSH).

10. The sampling assembly according to claim 1, wherein the hormone-specific antibody comprises an antibody specific for a hormone selected from the group consisting of estrogen, progesterone, luteinizing hormone (LH), and follicle stimulating hormone (FSH).

11. A method of making a sampling assembly for simultaneously testing a liquid biological sample for a plurality of hormones, the method comprising:
providing a sampling membrane comprising a dry porous carrier having a proximal end narrower than a distal end and forming a unidirectional liquid flow channel proceeding from the proximal end along a longitudinal axis to the distal end; the distal end of the sampling membrane comprising a plurality of tines arranged and separated by substantially regular spacing parallel to the longitudinal axis, each tine having a dye zone comprising a dye-tagged hormone-specific antibody at a distal end; wherein the sampling membrane further comprises a set of focusing recesses along each side of the unidirectional flow channel and a set of dispersal recesses between and adjacent to each tine; and
communicatively attaching each of a plurality of test strips to the distal end of each tine; each test strip comprising a dry porous carrier and forming a unidirectional liquid flow channel proceeding from the proximal end along the longitudinal axis and further comprising a testing zone comprising an immobilized hormone-specific antibody located distally from the dye zone of each tine.

12. The method according to claim 11, further comprising:
providing a casing comprising a substantially hollow cavity extending continuously along a longitudinal axis from a proximal end and sized to fixedly receive the sampling membrane and the test strips; the casing further comprising an aperture on the proximal end exposing the proximal end of the sampling membrane and disposed to facilitate liquid flow downstream along the unidirectional liquid flow channels.

13. The method according to claim 12, further comprising:
providing a cover comprising a substantially hollow cavity disposed to removably cover the exposed proximal end of the sampling membrane.

14. The method according to claim 12, further comprising:
forming an aperture window along a side of the casing that is disposed to provide visual inspection of the testing zone.

15. The method according to claim 12, further comprising:
forming at least one pylon within the hollow cavity near a distal end of the casing and fixedly holding the distal end of at least one test strip.

16. The method according to claim 12, wherein the casing comprises a moisture-impervious material.

17. The method according to claim 11, wherein each test strip further comprises a control zone comprising an antibody that is not specific for the hormones in the sample and that is located distally from the testing zone of each tine.

18. The method according to claim 11, wherein each focusing recess comprises a semi-circularly-shaped cavity and each dispersal recess comprises a semi-ovoidly-shaped cavity.

19. The method according to claim 11, wherein the dye-tagged hormone-specific antibody comprises an antibody specific for a hormone selected from the group consisting of estrogen, progesterone, LH, and FSH.

20. The method according to claim 11, wherein the hormone-specific antibody comprises an antibody specific for a hormone selected from the group consisting of estrogen, progesterone, luteinizing hormone (LH), and follicle stimulating hormone (FSH).

21. A multi-strip testing device for simultaneously assaying a liquid biological sample for a plurality of hormones, comprising:
a sampling assembly, comprising:
a sampling membrane comprising a dry porous carrier forming a unidirectional liquid flow channel proceeding from a proximal end along a longitudinal axis to a distal end, wherein the proximal end comprises a sampling zone and the distal end forms a shoulder wider than the proximal end and further comprises a set of focusing recesses along each side; the sampling membrane further comprising a plurality of tines arranged and separated by substantially regular spacing parallel to the longitudinal axis and comprising a set of dispersal recesses between and adjacent to each tine, each tine comprising a dye zone comprising a dye-tagged hormone-specific antibody at a distal end; and
a plurality of test strips, each test strip comprising a dry porous carrier communicatively attached to the distal end of each tine and arranged and separated by substantially regular spacing parallel to the longitudinal axis; wherein each test strip further forms a unidirectional liquid flow channel proceeding from the proximal end along the longitudinal axis and further comprises a testing zone comprising an immobilized hormone-specific antibody located distally from the dye zone of each tine; and
a casing comprising a substantially hollow cavity extending continuously along the longitudinal axis from a proximal end and sized to fixedly receive the sampling assembly; the casing further comprising an aperture exposing the sampling zone and disposed to facilitate liquid flow downstream along the unidirectional flow channels.

22. The multi-strip testing device according to claim 21, further comprising:
an aperture window formed along a side of the casing above the testing zone that is disposed to provide visual inspection of the testing zone during use.

23. The multi-strip testing device according to claim 21, further comprising:
a control zone on each test strip comprising an antibody that is not specific for the hormones in the sample and that is located distally from the testing zone of each tine.

24. The multi-strip testing device according to claim 21, wherein each focusing recess comprises a semi-circularly-shaped cavity and each dispersal recess comprises a semi-ovoidly-shaped cavity.

25. The multi-strip testing device according to claim 21, wherein the casing comprises a moisture-impervious material.

26. The multi-strip testing device according to claim 21, wherein the dye-tagged hormone-specific antibody comprises an antibody specific for a hormone selected from the group consisting of estrogen, progesterone, luteinizing hormone (LH), and follicle stimulating hormone (FSH).

27. The multi-strip testing device according to claim 21, wherein the hormone-specific antibody comprises an antibody specific for a hormone selected from the group consisting of estrogen, progesterone, luteinizing hormone (LH), and follicle stimulating hormone (FSH).

28. A method of making a multi-strip testing device for simultaneously assaying a liquid biological sample for a plurality of hormones, the method comprising:

providing a sampling assembly, comprising:

fashioning a sampling membrane comprising a dry porous carrier forming a unidirectional liquid flow channel proceeding from a proximal end along a longitudinal axis to a distal end, wherein the proximal end comprises a sampling zone; the distal end of the sampling membrane comprising a shoulder wider than the proximal end and further comprising a set of focusing recesses along each side; the sampling membrane further comprising a plurality of tines arranged and separated by substantially regular spacing parallel to the longitudinal axis and comprising a set of dispersal recesses between and adjacent to each tine, each tine comprising a dye zone comprising a dye-tagged hormone-specific antibody at a distal end; and communicatively attaching a plurality of test strips to the distal end of each tine in substantially regular spacing parallel to the longitudinal axis, each test strip further comprising a dry porous carrier and comprising a testing zone comprising an immobilized hormone-specific antibody located distally from the dye zone of each tine; each test strip further forming a unidirectional flow channel proceeding from the proximal end along the longitudinal axis; and constructing a casing comprising a substantially hollow cavity extending continuously along the longitudinal axis from a proximal end and sized to fixedly receive the sampling assembly; the casing further comprising an aperture exposing the sampling zone and disposed to facilitate liquid flow downstream along the unidirectional flow channels.

29. The method according to claim 28, further comprising:

forming an aperture window along a side of the casing above the testing zone that is disposed to provide visual inspection of the testing zone during use.

30. The method according to claim 28, wherein each test strip further comprises a control zone comprising an antibody that is not specific for the hormones in the sample and that is located distally from the testing zone of each tine.

31. The method according to claim 28, wherein each focusing recess comprises a semi-circularly-shaped cavity and each dispersal recess comprises a semi-ovoidly-shaped cavity.

32. The method according to claim 28, wherein the casing comprises a moisture-impervious material.

33. The method according to claim 28, wherein the dye-tagged hormone-specific antibody comprises an antibody specific for a hormone selected from the group consisting of estrogen, progesterone, luteinizing hormone (LH), and follicle stimulating hormone (FSH).

34. The method according to claim 28, wherein the hormone-specific antibody comprises an antibody specific for a hormone selected from the group consisting of estrogen, progesterone, luteinizing hormone (LH), and follicle stimulating hormone (FSH).

* * * * *